United States Patent [19]

Karol et al.

[11] Patent Number: 4,870,158

[45] Date of Patent: Sep. 26, 1989

[54] POLYMYXIN LIPOPOLYSACCHARIDE ANTIGEN AND ASSOCIATED METHOD

[75] Inventors: Meryl H. Karol; Lisa K. Ryan, both of Pittsburgh, Pa.

[73] Assignee: University of Pittsburgh of The Commonwealth System of Higher Education, Pittsburgh, Pa.

[21] Appl. No.: 118,213

[22] Filed: Nov. 5, 1987

Related U.S. Application Data

[63] Continuation-in-part of Ser. No. 000,489, Jan. 5, 1987, abandoned.

[51] Int. Cl.[4] .................. C07K 7/62; A61K 39/00; B01J 20/00; G01N 33/531
[52] U.S. Cl. ................... 530/319; 530/387; 424/88; 210/691; 502/400; 436/543
[58] Field of Search .............. 530/387, 319; 424/88, 424/92; 210/691; 502/400; 436/543

[56] References Cited

U.S. PATENT DOCUMENTS

| | | | |
|---|---|---|---|
| 4,057,685 | 11/1977 | McIntire | 536/18 |
| 4,185,090 | 1/1980 | McIntire | 424/92 |
| 4,225,487 | 9/1980 | Cuatrecasas et al. | 260/121 |

OTHER PUBLICATIONS

Chemical Abstracts, Laporte et al; Inhibition of *E. coli* Growth and Respiration by Polymyxin B Covalently Attached to Agarose Beads, vol. 87. p. 629h (1977).
Chemical Abstracts, Issekutz et al; Effect of Methylprednisolone and Polymyxin B Sulfate on Endotoxin-Induced Inhibition of Human Neutrophil Chemotaxis. vol. 90, p. 115598B (1979).
Carlsson et al., "Titration of Antibodies to *Salmonella* O Antigens by Enzyme-Linked Immunosorbent Assay", *Infection and Immunity*, vol. 6 (1972), pp. 703–708.
Holgrem, "Studies of Methods For Quantitation Of Agglutinens and Precipitins of *Escherichia coli* O and K Antigen", *Int. Arch. Allergy*, 37: 480–494 (1970).
Ekborg et al., "Artificial Disaccharide-Protein Conjugates As Immunogens For The Preparation of Specific Anti-Salmonella O-antisera", *Immunochemistry* 14: pp. 153–157 (1977).
Dufer et al., "Synthese d'ADN et Synthese d'anticorps dans les cellules spleniques de la Souris apres immunisation, in vivo, par le lipopolysaccharide d'*Escherichia coli*, modifie par la polymyxine B", *Comptes Rendus Hebdom Adai Res Des Sean Ces De L'Academie Des Sciences*, Series D vol. 290, pp. 699–701 (1980) and Translation.
Svenson et al., "Immunochemistry Of Salmonella O-Antigens: Preparation of An Octasaccharide-Bovine Serum Albumin Immunogen Representative Of *Salmonella* Serogroup B O-Antigen And Characterization Of The Antibody Response", *J. Immunology* 120(5): pp. 1750–1757 (1978).

*Primary Examiner*—Margaret Moskowitz
*Assistant Examiner*—Abdel A. Mohamed
*Attorney, Agent, or Firm*—Arnold B. Silverman

[57] ABSTRACT

Antigens that produce antibodies specific for the lipopolysaccharide or endotoxin are produced and characterized. A method of producing the antigen is disclosed. These specific antibodies may be used as immunodiagnostic agents to detect the presence of and quantity of endotoxin in samples.

8 Claims, 6 Drawing Sheets

POLYMYXIN LIPOPOLYSACCHARIDE ANTIGEN AND ASSOCIATED METHOD

CROSS REFERENCE TO RELATED APPLICATION

This application is a continuation-in-part of Application Serial No. 07/000,489, entitled "POLYMYXIN AGAROSE-LIPOPOLYSACCHARIDE ANTIGEN AND ASSOCIATED METHOD", filed Jan. 5, 1987 now abandoned.

BACKGROUND OF THE INVENTION

The present invention relates to a polymyxin lipopolysaccharide antigen that creates antibodies that detect endotoxin and the method of making the antigen.

The invention described herein was supported in part by Cooperative Agreement 58-48YK-5-0050 from the United States Department of Agriculture.

1. Field of the Invention

This invention relates to the production and characterization of antigens that create antibodies specific for endotoxin and more specifically, the antigen and the antibodies, and use of these specific antibodies as an immunodiagnostic reagent to detect endotoxin.

2. Description of the Prior Art

Bacterial contamination is currently one of the leading causes of fatal bacterial infection. Endotoxin is known to cause toxic effects in multiple cell types and organs. Endotoxin is responsible for the symptoms associated with byssinosis, septicemia, bacteremia, and the like. These symptoms may include fever, diarrhea, hemorrhagic shock, tissue damage, bronchospasms, damage to endothelial cells and the like. Release of endotoxin into the blood stream may cause endotoxin shock as well as other systemic effects.

Endotoxin is a component of the cell wall of Gram negative bacteria. The cell wall of Gram negative bacteria is multilayered and quite complex. Endotoxin is composed of lipid A and a polysaccharide. Lipid A is the core material. The polysaccharide is exterior of the lipid A. The polysaccharide component is unique to each type of bacterium.

Assays to detect endotoxin activity have received great attention. Among the procedures currently in use to analyze solutions for endotoxin activity are the *Limulus* amebocyte lysate assay (LAL) and the USP rabbit test for pyrogenicity.

The LAL assay measures endotoxin by detecting only one biological activity of endotoxin in a highly purified sample. The LAL measures the ability of lipopolysaccharide to gel or precipitate the lipote. Results from the assay do not correlate with the ability of endotoxin to cause respiratory toxicity in animals or nuetrophil chemotaxis in human beings. Difficulties encountered with the LAL assay include interference by numerous organic compounds yielding both false-positive and false-negative results, as well as an inability to correlate consistently with the USP rabbit pyrogen test.

The rabbit pyrogen test involves injecting a rabbit with a sample suspected of endotoxin toxicity. The temperature of the rabbits is measured for a period of time. If a fever is produced in the rabbit, the presence of endotoxin is indicated. A gross estimate of the amount of endotoxin can be determined by the rise in temperature of the rabbit. The USP rabbit test for pyrogenicity is expensive and the results are not always accurate.

Recent attempts to quantify the endotoxin content of biological solutions have employed immunologic assays. The relatively poor immunogenicity of lipopolysaccharide compared to protein antigens has led to use of lipopolysaccharide (LPS) complexes for immunization. Several endotoxin immunizing agents are known. See, for example, U.S. Pat. Nos. 4,057,685 and 4,185,090.

Polyclonal antibodies have been produced to wild-type LPS by immunizing rabbits intravenously with heat-killed bacteria. See Carlsson et al, "Titration of Antibodies to *Salmonella* O Antigens by Enzyme-Linked Immunosorbent Assay" *Infection and Immunity*, Volume 6 (1972) pp. 703–708; Holmgren "Studies of Methods For Quantitation of Agglutinens and Precipitins of *Escherichia Coli* O and K Antigen" *Int. Arch. Allergy*, Volume 37 (1970) pp. 480–494. Additionally, covalent linking of the disaccharide antigenic determinants to bovine serum albumin (BSA) has also resulted in high titered antisera. See Ekborg et al "Artificial Disaccharide-Protein Conjugates As Immunogens For The preparation Of Specific Anti-*Salmonella* O-antisera" *Immunochemistry*, Volume 14 (1977) pp. 153–157. However, in using these procedures, antibodies were also produced to BSA or cell membrane components.

Dufer et al "Synthese d'ADN et Synthese d'anticorps dans les cellules spleniques de la Souris apres immunisation, in vivo, par le lipopolysaccharide d'*Escherichia coli*, modifie par la polymyxine B" *Comptes Rendus Hebdom Adai Res Des Sean Ces De L'Academie Des Sciences*, SERIES D VOLUME 290 (1980), pp. 699–701 disclose an antigen using a complex of LPS and polymyxin B which induces spleen cells which are said to recognize LPS.

Methods of obtaining high titered, specific antibody have not been adequate for development of a sensitive specific serological assay for endotoxin. At present there is lacking an effective immunodiagnostic test which detects the presence and amount of endotoxin in biological materials with sensitivity.

There remains, therefore, a very real and substantial need for an antigen and a process for producing and characterizing the antigen that produces antibodies specific for endotoxin, and an antibody which will detect endotoxin from bacterial species, as well as producing these antibodies in large quantities and at a low cost for use in immunodiagnostic tests to achieve highly sensitive results.

SUMMARY OF THE INVENTION

The present invention provides antigens that produce antibodies that are specific for the lipopolysaccharide in endotoxin. A method of producing the antigen and the antibodies is also disclosed. Further, immunodiagnostic assays using these antibodies are also disclosed.

The antigen is produced by a polymyxin B-matrix complex (PMC) which is mixed with and which binds to free lipopolysaccharide. The polymyxin B-matrix-LPS complex is separated from uncomplexed materials by centrifugation and then washed.

The use of the LPS polymyxin-B matrix antigen for immunization of animals yields a high titer of antibody. In contrast to other methods which have utilized LPS complexes for immunogens, the antibodies of the present invention are highly specific for the LPS portion of the complex and do not react with the polymyxin B component. This procedure produces antisera which detects and quantifies the amount of endotoxin in biological fluids.

Hybridomas secreting monoclonal antibodies specific for endotoxin can be produced by fusion of myeloma cells with spleen cells from mice immunized with purified endotoxin. Hybridomas secreting antibodies specific for endotoxin were selected and cloned. These hybridomas were then grown as ascitic tumors in mice and monoclonal antibodies were purified from the ascites fluids. Alternatively, the hybridomas may be grown in mass culture.

It is an object of the present invention to provide a method of producing an antigen that or induces antibodies specific for endotoxin.

It is an object of the present invention to provide an antigen that produces antibodies in vivo that are specific for lipopolysaccharide or endotoxin.

It is a further object of the present invention to provide an antigen that produces monoclonal antibodies in vitro which are specific for lipopolysaccharide or endotoxin.

It is another object of the present invention to provide a method of using the antibodies specific for endotoxin in an immunodiagnostic assay for the detection of the presence of the endotoxin.

It is a further object ot the present invention to provide a means to quantify the antibodies specific to the lipopolysaccharide in a specimen.

It is an object of the present invention to provide hybridomas that secrete monoclonal antibodies specific for endotoxin.

These and other objects of the invention will be more fully understood from the following description of the invention with reference to the illustrations appended hereto.

DESCRIPTION OF THE PREFERRED EMBODIMENTS

Figure 1:
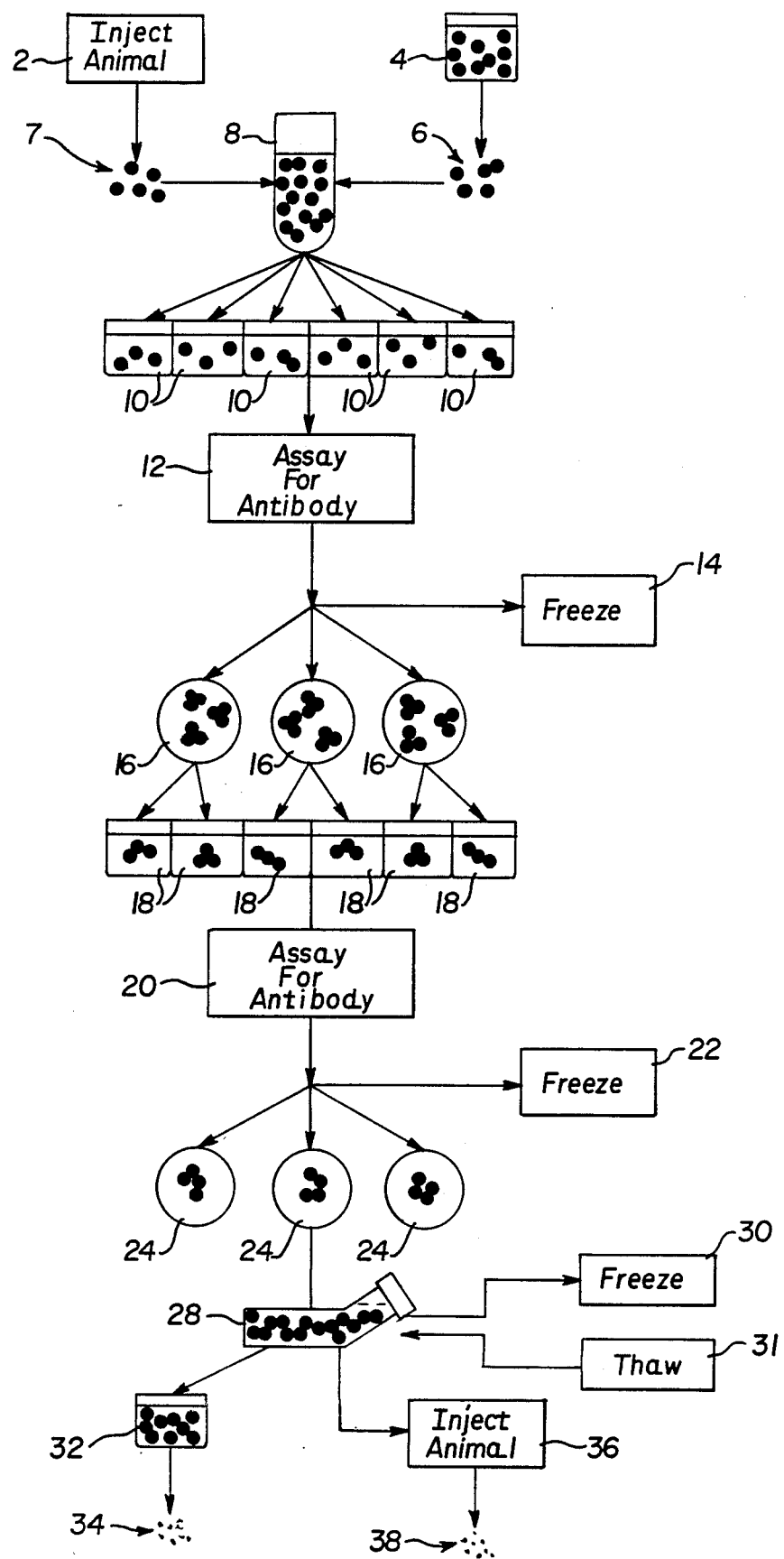
FIG. 1 is a schematic illustration of a method of making monoclonal antibodies of the present invention.

The present invention discloses an antigen which produces antibodies that are specific for lipopolysaccharide or endotoxin; a method for producing antigen that induces antibodies that are specific for the lipopolysaccharide or endotoxin and diagnostic tests using these antibodies is also disclosed.

A method of producing the antigen involves mixing a specific free LPS, such as a Gram-negative bacterial endotoxin (LPS), with polymyxin B immobilized on a matrix for about 5 minutes to 24 hours at about 4° C. to 37° C. The LPS-polymyxin B-matrix complex is centrifuged to separate the complex from the supernatant which contains free LPS and then washed preferably with saline. The complex is emulsified with an immunostimulatory agent, such as Freund's Complete Adjuvant, and injected into an animal, such as guinea pigs, mice, rats, and the like. The immunogen stimulates the production of high titer antisera specific for the LPS moiety.

The specificity of antibodies was investigated using ELISA inhibition. Antibodies were highly specific for the immunizing LPS and showed no cross-reactivity with heterologous endotoxin. The high titer of antibody produced following a single injection indicates that the method produces a strong immunogenic stimulus such as that required for production of monoclonal antibodies.

Polymyxin B is a peptide antibiotic which contains a cationic cyclopeptide ring with a 7 or 8 carbon fatty acid attached through an amide bond. Polymyxin B has been shown to bind electrostatically and possibly hydrophobically to LPS. This property has been utilized to neutralize the biological effects of endotoxin in vivo and to render solutions endotoxin-free. Polymyxin B has a high affinity for endotoxin.

It is preferred that the matrix be insoluble in an aqueous medium and be capable of binding to or reacting with Polymyxin B. The matrix may be composed of synthetic, natural, or polymeric materials, such as resinous materials, such as plastics, for example, polyethylene, polypropylene, polystyrene and the like, cellulose, nitrocellulose, dextran, fibrous materials, such as graphite, asbestos, nylon and the like, for example.

The most preferred matrix is agarose. Agarose is a natural seaweed product. It is in the form of an insoluble gel. Agarose swells in water. Agarose has chemical groups on its surface to which proteins can be attached.

A preferred method of making the polymyxin B-agarose complex (PAC) uses agarose beads. Agarose beads such as Affi-Gel 10 are an agarose derivative with added aliphatic arms about 10A in length, terminated with an active carboxy-N-hydroxysuccinimide ester. The polymyxin B is covalently attached to the arms and suspended in a preservative, such as 50% glycerol and 0.5% sodium azide.

Free lipopolysaccharide is a bacterial extract which may be obtained from the bacterial wall using solvents such as phenol, chloroform, petroleum ether, butanol, trichloroacetic acid and the like, and purified. The polysaccharide component in the bacterial cell wall is unique to each type of bacteria. Examples of microorganisms that contain endotoxin include Pseudomonodaceae, Azotobacteraceae, Rhizobiaceae, Methylomonadaceae, Halobacteriaceae, Acetobacteria, Enterobacteriaceae, Bibrionaceae, Bacteroidaceae, Neisseriaceae, Veillonellaceae, Nitrobacteraceae, Siderocassaceae, and the like. More specifically, LPS may be obtained from *Escherichia coli*, *Salmonella minnesota*, *Pseudomonas syringae*, *Enterobacter agglomerans*, *Klebsiella pneumonia*, and the like.

Polymyxin B binds LPS very well by electrostatic interaction with possibly some contribution from hydrophobic interaction. The matrix, which is bonded to polymyxin B, helps to purify the antigen. Due to the insolubility of the matrix, it functions to pull the LPS bound to polymyxin out of solution.

The preferred method of producing a hybridoma antibody is best illustrated by reference to FIG. 1. An animal is injected with LPS-PMC 2. The spleen of the animal is removed. During this time, myeloma cells 4 are cultured. The spleen cells 7 and the myeloma cells 6 are fused in the presence of a fusion promoter, preferably in polyethylene glycol 8 for about 2 hrs. at 37° C. The fused cells are then placed in a medium that will not support unfused cells 10, preferably HAT medium, for selection. Cells that have successfully fused, also known as hybrids, are selected by the HAT medium. The hybrid cells are assayed for the presence of antibody secretion 12. The preferred assay is an ELISA assay. Optionally, a portion of each positive culture may be frozen 14. Positive cultures are then cloned 16. Cloning may be done either by limiting dilution or by placing the positive cultures into mice and grown. The cells are then cultured in HAT medium and selected again 18. The positive cultures are then assayed for the presence of the antibody 20. The preferred assay is the ELISA assay. Optionally, sections of the positive cultures may be frozen 22. The positive cultures are recloned 24 and analyzed to select variants. The clones 28 finally selected are grown. Alternatively, they may be frozen and thawed. At this point the hybridomas may be grown in mass culture 32, thereby producing the desired monoclonal antibody 34. Alternatively, an animal such as a guinea pig, mouse, or rat may be injected with the hybridoma 36 to induce myelomas that secrete the antibody 38.

The above-described antigen and antibodies may be used in a diagnostic test to determine the presence of endotoxin in a specimen, for example, human secretions, urine, food, blood, serum, and the like. Due to the specificity of the antibodies, the samples do not have to be purified when using the diagnostic tests. The antigen and antibodies may be used to detect the presence of endotoxin in pharmaceuticals of any type and medical devices, such as hemodialysis membranes, plasma fractionation devices, and catheters and the like. The antibody may be immobilized on a filter to determine the presence of endotoxin in the air.

The antibody may be incorporated into an immunodiagnostic test, such as an ELISA, RIA and the like, and the endotoxin detected by competitive inhibition assay. In the case of the ELISA, samples of suspected endotoxin material are placed in at least some of the wells of assay plates, previously coated with endotoxin, and incubated, then washed with buffer. Antibody is added to the wells and allowed to react. The wells are washed again. An anti-immunoglobulinenzyme is added to the wells and allowed to react with the monoclonal antibody. The enzyme portion may be, for example, horseradish peroxidase, or alkaline phosphates. The wells are washed. A chromogenic substrate, such as p-nitrophenyl phosphate, o-dianisidine with hydrogen peroxide, 5-aminosulfacylic acid with hydrogen peroxide, 2,2,-azinodi(3-ethyl benzthiazoline sulfonic acid) (ABTS) with hydrogen peroxide for example, is added to each well and then allowed to react. The reaction is stopped, the color of the chromogen may be measured visually or spectrophotometrically to determine the presence and quantity of endotoxin.

Alternatively, a plate having 96 wells may be coated with antibody incubated and washed. Excess binding sites on the plates may be blocked with a blocking solution containing heterologous proteins such as bovine serum albumin or milk proteins. The blocking solution is removed and the well is washed. Samples containing the suspected endotoxin are added to the wells and incubated. The plates are washed. The antibody to which an enzyme such as horseradish peroxidase or alkaline phosphates has been attached is added to the wells and reacts with the bound endotoxin. The wells are washed and conjugate is added. The chromogenic substrate such as 0.1% p-nitrophenyl phosphate, 10% diethanolamine, 0.01% $MgCl_2$, pH 9.6 in the example of alkaline phosphatase is added and the reaction is stopped with any strong basic compound which raises the pH high enough to inactivate the enzyme by denaturation. Results may be read visually or spectrophotometrically to show the presence and quantity of endotoxin.

Figure 2A:
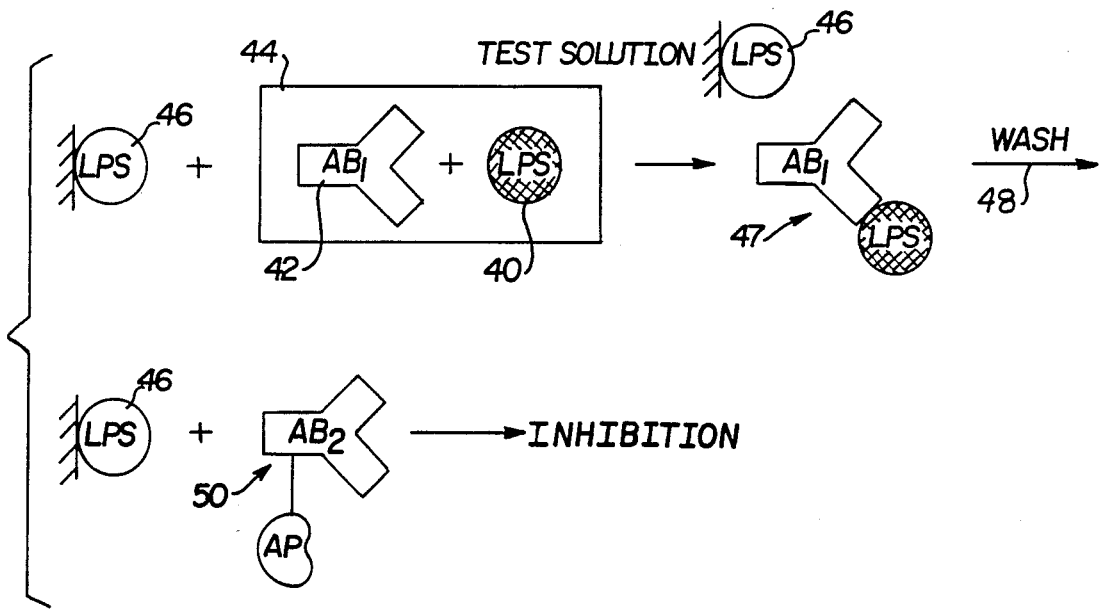
FIGS. 2a and 2b are schematic illustrations of a competitive ELISA procedure of the present invention.
Figure 2B:
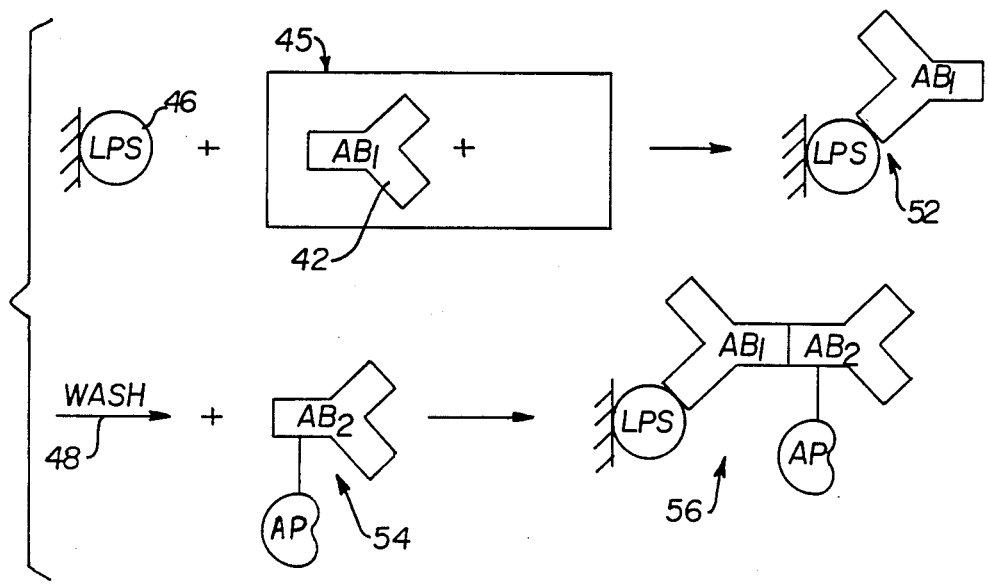

A competitive ELISA procedure may also be used. This procedure is illustrated in FIGS. 2a and 2b. A solution of suspected endotoxin 40 or LPS in 0.02M phosphate buffer is placed in a test tube with antibody 42. This test solution 44 is then added to wells precoated with LPS 46. If endotoxin is present in test solution 44, the antibody will bind to the andotoxin 47. The antibody 42 also binds to the LPS coated on the plate 46, but when endotoxin is present in the solution, there is competition for the antibody 42. The plate 42 is washed with phosphate buffer 48 removing the bound endotoxin and antibody 47 present. An enzyme substrate which is hydrolyzed by the enzyme is then added to the wells 50. The amount of color produced by addition of a chromogenic substrate which binds to the enzyme indicates the presence and quantity of endotoxin.

In FIG. 2b, endotoxin is not present in the test solution 45, the procedure is followed as described hereinabove, but in this case, the antibody 42 is bound to the LPS on the plate 52. The plate is washed 48. When the enzyme substrate 54 is added, it binds to the antibody 56. A chromogenic substrate is added. The color developed is more intense due to the lack of endotoxin present in the test solution competing for the antibody.

Figure 3A:
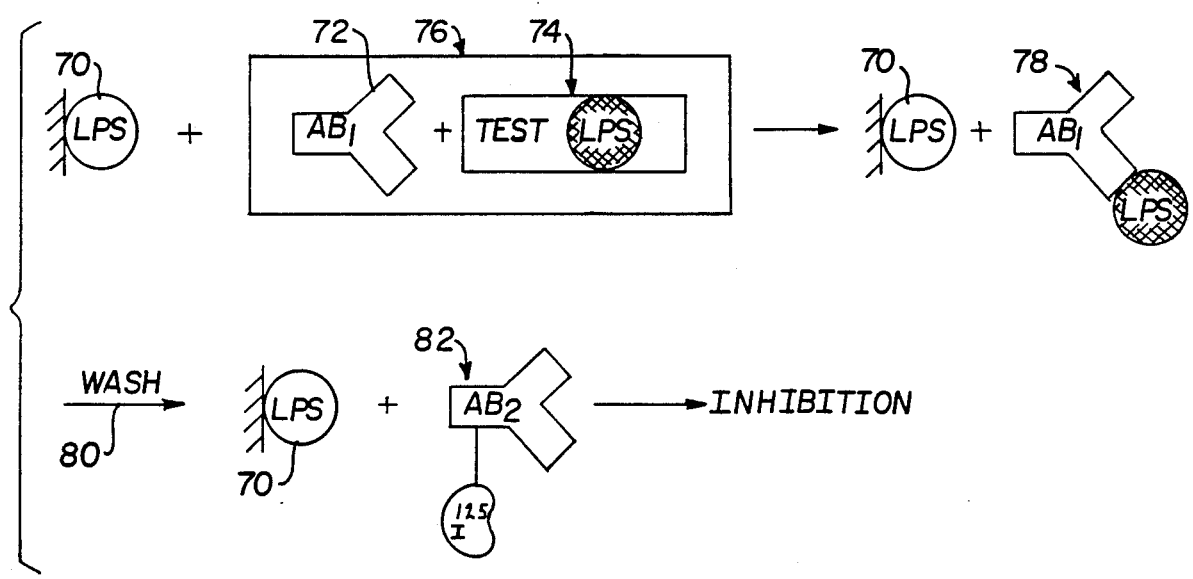
FIGS. 3a and 3b are schematic illustrations of a competitive RIA procedure of the present invention.
Figure 3B:
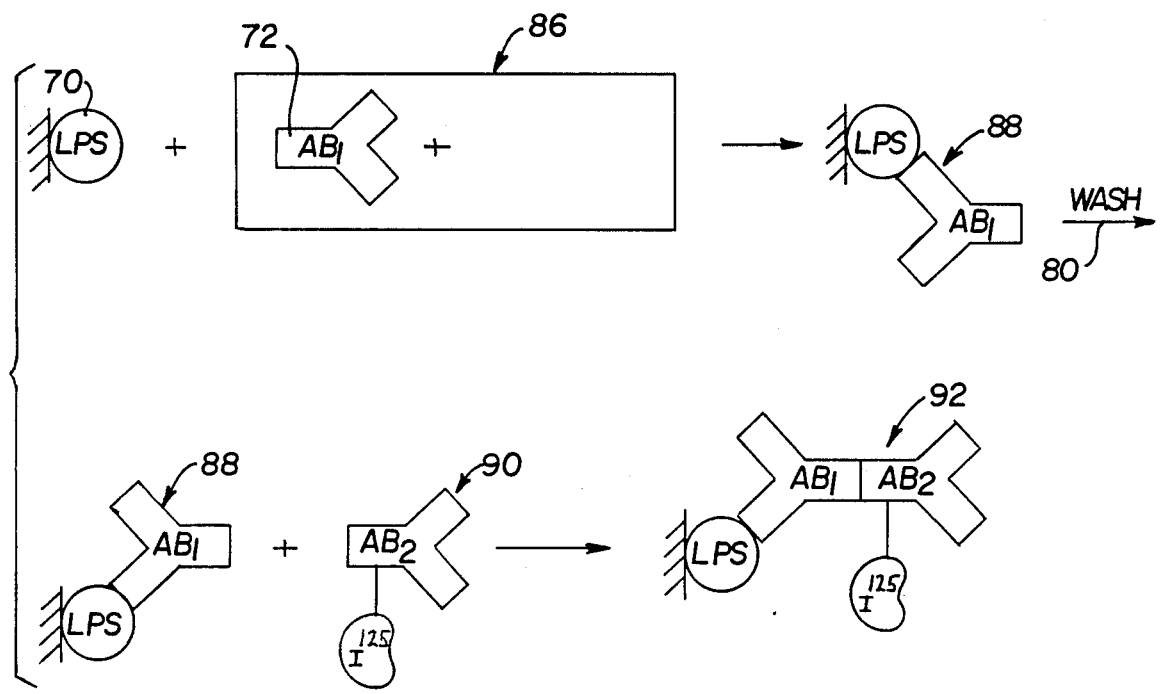

An analogous system can be used with an RIA, as shown in FIGS. 3a and 3b. Endotoxin or LPS may be adsorbed to a solid medium 70, such as a paper disk and the above procedure followed. As shown in FIG. 3a, endotoxin is present in the test solution 74 which contains antibody 72. The antibody binds to the endotoxin in solution 78. The antibody also binds to the bound LPS (not shown), but the bound LPS is competing with the endotoxin in the test solution for the antibody. The plate is washed 80, thereby washing away the bound antibody and endotoxin in the test solution. $I^{125}$-antibody 82 is then added and allowed to react with the bound antibody. If there is no endotoxin present in the test solution as in FIG. 3b, the antibody 72 binds to the LPS bound to the plate 88. When the labeled antibody 90 is added, it binds to the antibody complex 92. After washing, the amount of radioactivity bound to each solid medium may be measured using a gamma scintillation counter. In the case of endotoxin presence, the amount of $I^{125}$-antibody bound to the plates is inhibited. If no endotoxin is present in the test solution as shown in FIG. 3b, the level of radioactivity is higher.

Other variations in performing a competitive immunoassay are also possible. For example, a known quantity of $I^{125}$-antibody can be added so a LPS-plate in the presence of an unknown amount of test antibody. The ability of the test antibody to compete with the $I^{125}$-antibody indicates the amount of antibody in the test solution.

EXAMPLE

Antigen Preparation

*E. coli* 055: B5 LPS (Difco Laboratories, Detroit, MI) was coupled to polymyxin B-agarose (Sigma Chemical Company, St. Louis, MO) using the following procedure. A 10 ml polymyxin B-agarose suspension of beads was washed to rid the polymyxin B-agarose beads of the glycerol and sodium azide preservative, resulting in about 5 ml of polymyxin B and agarose. One ml of a 10 mg/ml solution of *E. coli* 055: B5 LPS in pyrogen-free sterile water (Abbott Laboratories, North Chicago, IL) was mixed with the polymyxin B-agarose beads. Assuming a total amount of 660 μg polymyxin B per gram of bead, the LPS was added in greater than 10 fold excess. The mixture was rocked gently overnight at 4° C. The LPS polymyxin B-agarose complex was centrifuged at 470× g for 10 min., then washed twice with 0.9% saline. Fir immunization, the gel was mixed with a small amount of saline and then emulsified with Freund's Complete Adjuvant (Difco Laboratories, Detroit MI).

Immunization Procedure

Five male English smooth-haired guinea pigs obtained from Hilltop Lab Animals, Inc., Scottdale, PA weighing 250-300 g were injected into each footpad with 50 μl LPS-polymyxin B-agarose emulsion described above. Blood samples were obtained prior to immunization and on day 29. Animals were anaesthetized with 10 mg Ketamine-HCl (Parke-Davis, Morris Plains, NJ) for cardiac bleedings. On day 29, a booster immunization was given using 2.2 ml of the LPS-polymyxin B-agarose emulsion mixed with 1.0 ml of pyrogen-free water and 1.5 ml of mineral oil. Each animal received 75 μl of this emulsion via a subcutaneous injection in the neck. After 11 days, serum samples were taken by cardiac puncture twice weekly for three weeks.

Immunobinding Procedure

Serum samples were screened for antibody to *E. coli* 055: B5 LPS using an immunobinding assay. LPS from *Escherichia coli* 055: B5 was adsorbed onto nitrocellulose paper discs (0.45 μm Bio-Rad Laboratories, Richmond, CA) using the following adsorptive immobilization technique.

Ten μl of 1 mg/ml LPS solution in pyrogen-free water was drawn onto 1 cm diameter nitrocellulose discs, using a 1 mm diameter pipette and vacuum-filtered. Ten μl of 1 mg/ml polymyxin B solution in pyrogen-free water was applied in a similar manner. Each disc was placed in a well of a 20 well tissue culture plate for the immunobinding procedure. The unbound sites on the nitrocellulose discs were blocked by incubating each disc for 2 hrs. at room temperature in phosphate buffered saline (pH 7.6) containing 3% bovine serum albumin (BSA), and then incubating the discs for 1 hr in PBS containing 1% BSA and 1% normal rabbit serum. The blocked discs were then washed three times. Test serum (diluted 1:5) was added to each disc. After shaking the discs for about 2 hrs. at room temperature they were washed four times. Rabbit anti-guinea pig IgG (H+L)-horseradish peroxidase conjugate (Miles Scientific, Naperville, IL) (1:100) was then added and incubation continued for about 2 hrs. at room temperature. The discs were washed three times. One ml of 4-chloro-1-naphthol hydrogen peroxide substrate solution was then added. The discs were incubated for 5 mins. Following visualization of color by eye, the substrate solution was removed and the discs stored at 4° C. in distilled water. Reaction was visualized for at least 3 months.

Figure 4:
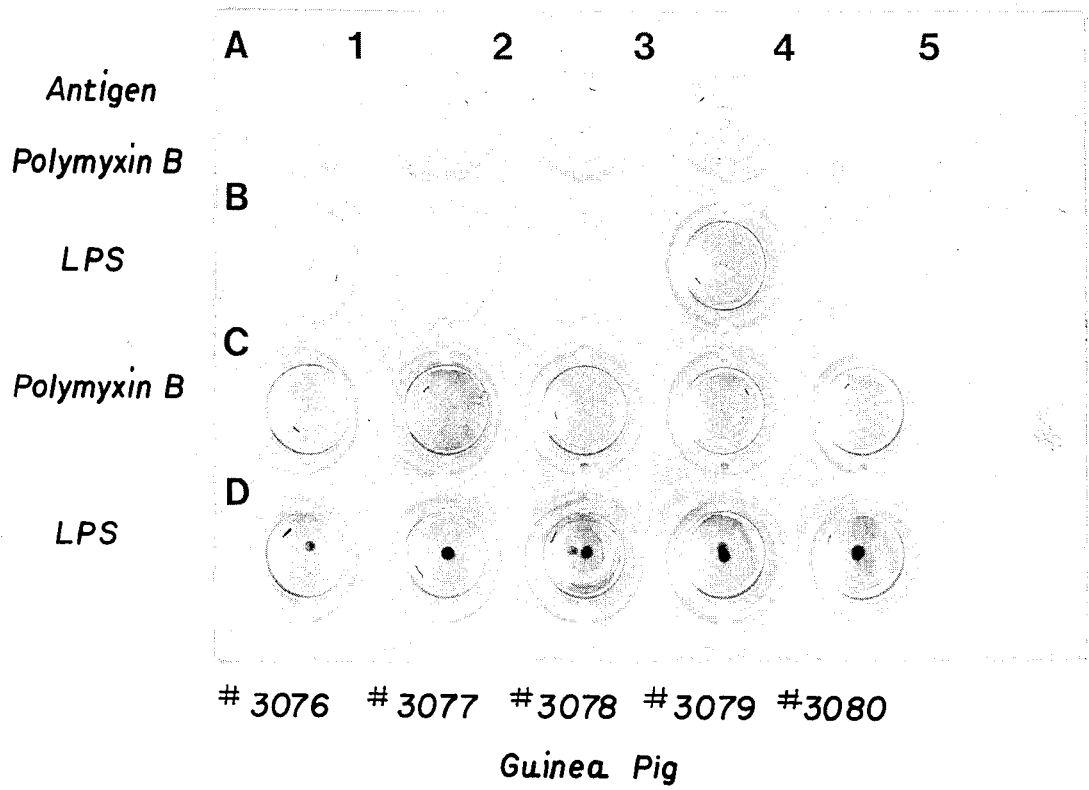
FIG. 4 is a photograph of a Dot-Immunobinding of sera from E. coli 005: B5 lipopolysaccharide polymyxin B-agarose complex (LPS-PAC).

FIG. 4 shows dot immunoblotting of sera from *E. Coli* 055: B5 LPS-PAC immunized guinea pigs. Rows A and B had preimmunized sera. Rows C and D had immune sera from day 29. FIG. 4 indicates a positive reaction on nitrocellulose discs containing *E. coli* 055: B5 LPS antigen and immune serum from each of the 5 guinea pigs (row D). No staining was obtained with any of the pre-immunization sera (rows A and B) or with discs containing the polymyxin B carrier (row C).

ELISA

Antibody titers were determined using the following ELISA procedure. Wells of Nunc Immunoplate I (high binding capacity microtitration plates, Nunc Intermed, Inc., Kamstrup, Denmark) were coated by using antigen solution in 0.1M sodium carbonate-bicarbonate buffer at pH 9.6. Plates were washed 3 times with saline tween (0.85% NaCl and 0.05% Tween 20). Serum in PBS-Tween containing 0.5% BSA was added to the plates. The plates were incubated for 2 hrs. at 37° C. The presence of IgG antibody was determined using rabbit anti-guinea pig IgG (H+L) alkaline phosphatase conjugate (Miles Scientific, Naperville, IL). After incubation at room temperature for 16 hrs., the enzyme was assayed using disodium p-nitrophenylphosphate (Sigma Chemical Co., St. Louis, MO) in 1M diethanolamine and 0.5 mM $MgCl_2$. Following reaction for 30 mins. at 37° C., 100 μl of 1M NaOH were added and the optical density was read at 410 nm using an MR 600 Microplate reader (Dynatech Laboratories, Inc., Alexandria, VA).

The titer of antibody in each serum was determined using ELISA. Microtiter plates coated with 0.001-50 μg/ml polymyxin B showed no titer in 4 of 5 animals. One animal had a titer of 1:1: only when 50 μg/ml of antigen was used to coat the plates.

Figure 5:
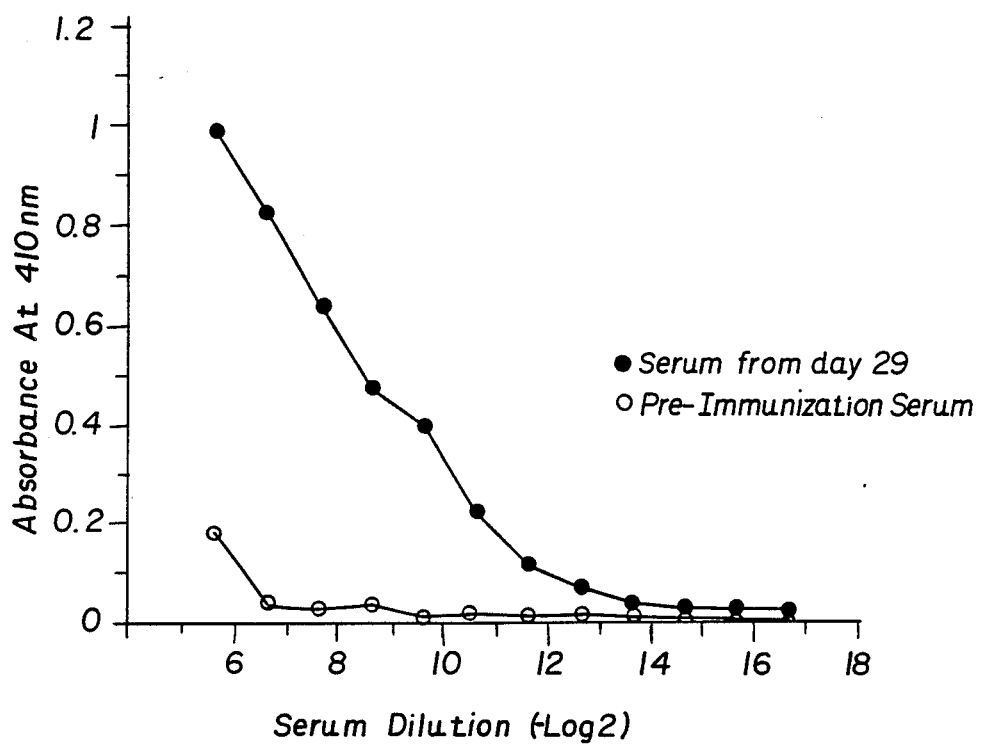
FIG. 5 is a plot of an ELISA assay of sera from a guinea pig immunized with E. Coli 055: B5 LPS-PAC titrated with homologous LPS.

To detect antibody to LPS, microtiter plates were coated with 0.01 to 10 μg/ml LPS. The optimal concentration of LPS to detect antibody was determined to be 10 μg/ml. Using this concentration, the antibody content of serial serum dilutions for one animal following a booster immunization is shown in FIG. 5. As calculated from FIG. 5, the titer of this serum was 1:3200. Each of the other four guinea pigs gave similar absorbance curves.

Figure 6:
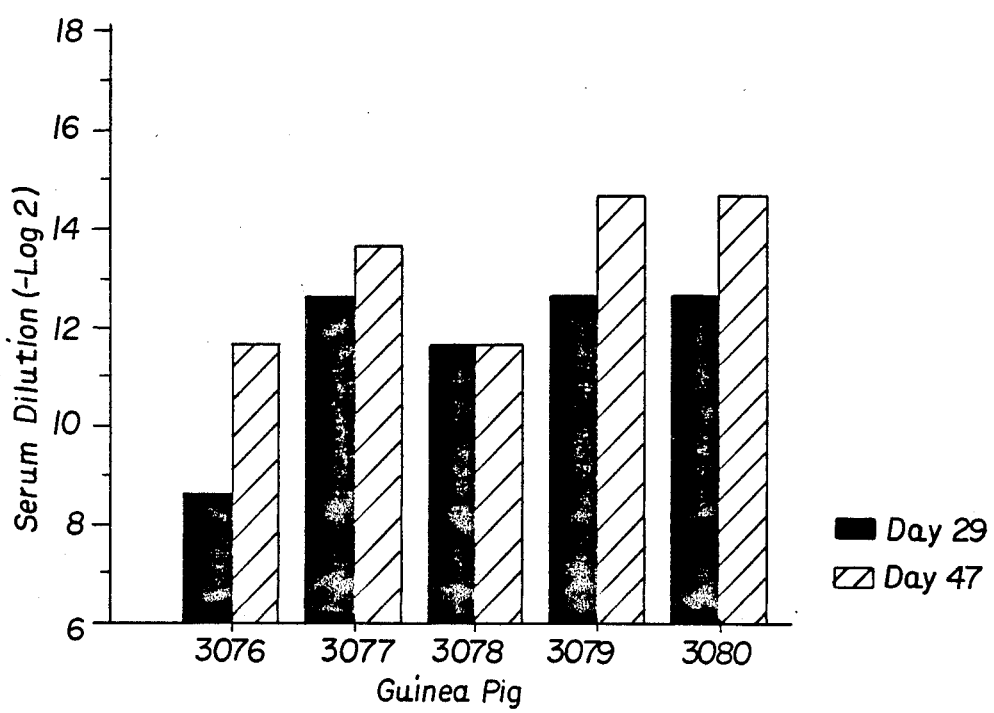
FIG. 6 is a plot of IgG titers of anti-sera from five guinea pigs immunized with E. Coli 055: B5 LPS-PAC as determined by ELISA.

Final titers for each of the animals prior to and following the booster immunization are shown in FIG. 6. FIG. 6 shows blood obtained before booster immunization (Day 29) and following the booster immunization (Day 47). Before the booster immunization, the highest titer in the three animals was 1:6400. The booster immunization increased this titer in two of these animals to 1:25,000 and also increased the LPS-specific antibody titer in another animal from 1:400 to 1:3200. In the two remaining animals, the booster immunization had little or no effect.

ELISA Inhibition Assay

The specificity of the antibody was evaluated using an ELISA inhibition assay. Sources of inhibitors were *E. coli* 055: B5 (obtained from Difco Laboratories, Detroit, MI) *E. coli* 0111: B4, *E. coli* J5, *Salmonella abortus equi*, and *Salmonella minnesota* Re595 (all obtained from Sigma Chemical Company, St. Louis, MO). The assay was similar to the ELISA method described hereinbefore. The dilution of antiserum used was that which gave an absorbance of 0.25 in the ELISA. The amount of inhibitor added to each well was varied. This amount ranged from 0.01 μg to 50 μg per well. Assays were performed in triplicate.

ELISA inhibition was used to evaluate the specificity of the antibodies and to determine whether antibodies were directed toward the lipid A region of the LPS molecule or to the sugar moieties.

Figure 7:
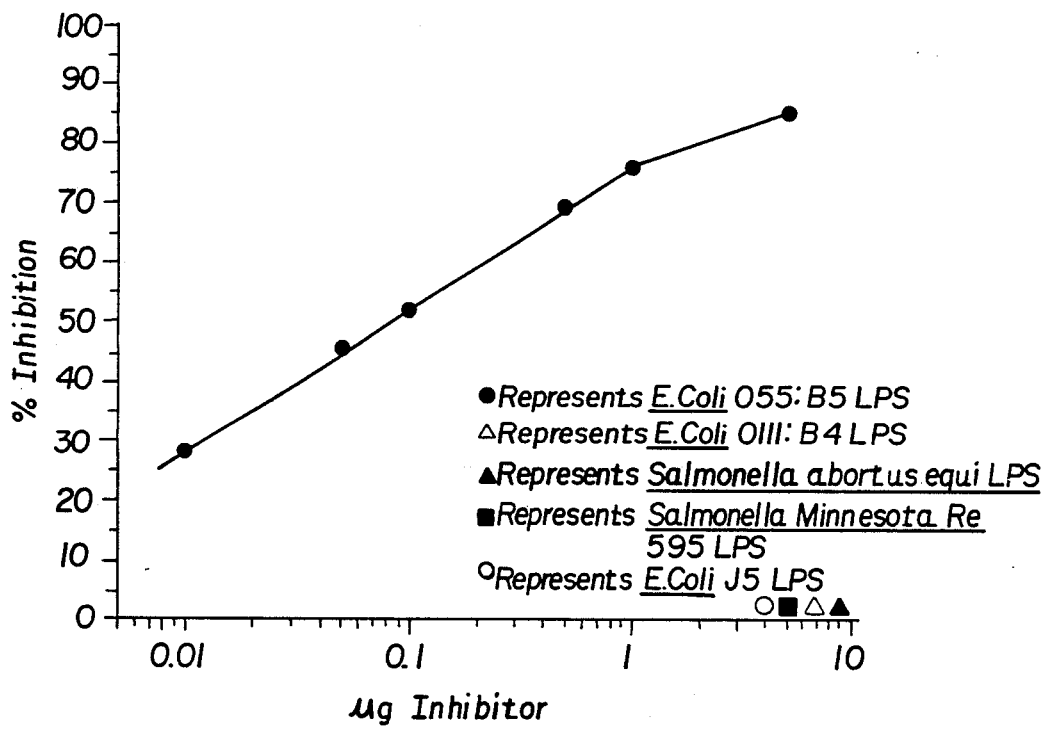
FIG. 7 is a graph of an ELISA Inhibition Assay of antiserum raised against E. Coli 055: B5 LPS-PAC using LPS from various Gram-negative species of bacteria.

FIG. 7 illustrates a typical ELISA inhibition curve. Serum from guinea pig 4 obtained on day 47 showed specificity for the homologous E. coli O55: B5 LPS. The amount of inhibition increased with increased amount of E. coli O55: B5 LPS inhibitor from 0.01 μg to 5 μg. No inhibition was observed when LPS from E coli O111: B4, E. coli J5, Salmonella minnesota Re595, or Salmonella abortus equi were used in the system, indicating specificity for the E. coli O55: B5 LPS.

Table 1 summarizes the amount of inhibitor required to produce 50% inhibition in three antisera obtained before the booster immunization. Inhibition was obtained using 70–495 ng E. coli O55: B5. By contrast, up to 50,000 ng of heterologous LPS could not produce any inhibition. These results indicated a high specificity of the antisera for the homologous LPS.

TABLE 1

Inhibition Of The E. coli O55:B5 LPS ELISA
ng Required For 50% Inhibition Of Specific Antibody Binding
For Each Individual Guinea Pig Serum*

| Type of LPS Inhibitor | Guinea Pig 2 | Guinea Pig 3 | Guinea Pig 4 |
|---|---|---|---|
| Escherichia coli O55:B5 | 416 | 459 | 70 |
| Escherichia coli O111:B4** | 50,000 | 50,000 | 50,000 |
| Escherichia coli J5** | 50,000 | 50,000 | 50,000 |
| Salmonella minnesota Re595** | 50,000 | 50,000 | 50,000 |
| Salmonella abortus equi** | 50,000 | 50,000 | 50,000 |

*The amount of inhibitor required to effect 50% inhibition of binding was determined from concentration-response lines on sera obtained on day 29.
**No inhibition was observed using up to 50 μg inhibitor.

The specificity of the antisera after the booster immunization was examined. In animals 3–5, the amount of inhibitor required did not change significantly after the booster immunization (Table 2). In animals 1 and 2, the specificity increased, since there was approximately a ten-fold decrease in the amount of inhibitor required to produce a 50% inhibition of response. No reactivity of antisera with polymyxin B was observed.

TABLE 2

Amount Of E. coli O55:B5 LPS Required For 50%
Inhibition Of The Homologous LPS ELISA For Each Guinea Pig
Antiserum Before And After The Booster Immunization

| | Amount Of E. coli O55:B5 LPS Inhibitor (ng) | |
|---|---|---|
| Guinea Pig | Day 29 | Day 47 |
| 1 | 4,560 | 363 |
| 2 | 416 | 25 |
| 3 | 459 | 307 |
| 4 | 70 | 84 |
| 5 | 1,350 | 1,690 |

E. Coli O55: B5 LPS was diluted with 0.1M carbonate buffer, pH 9.6 to a concentration of 10 μg/ml. 100 μl of the LPS solution was added to each well of a 96 well polystyrene plate. The plate was incubated for 3 hours at 37° C., then incubated over night at 4° C. The plate was washed three times for three minutes with Tween-Saline.

Antisera were diluted 1:100 in PBS-Tween BSA buffer, pH 7.4, and two fold dilutions were made in PBS-Tween-BSA buffer up to 204,800. A test solution containing endotoxin was added. The diluted antisera and test solution were incubated in the wells for 2 hours at 37° C. The plates were then washed three times for three minutes each with Tween-Saline.

Rabbit anti-guinea pig IgG (H+L)-alkaline phosphatase enzyme conjugate was diluted 1:800 in PBS-Tween. 100 μl was placed in each well and incubated overnight at room temperature. The plates were washed three times for three minutes each with Tween-Saline. Color was developed adding 100 μl of a 1 mg/ml substrate solution of p-nitrophenyl phosphate in 1M diethanolamine and 0.5 mM $MgCl_2$ and incubated in each well for 30 minutes at 37° C. The reaction was stopped by addition of 100 μl per well of 1N sodium hydroxide. The results were determined using an ELISA spectrophotometer at 410 nanometers.

It will be appreciated that the LPS-polymyxin B-agarose antigen produced antibodies specific for the LPS from E. Coli O55: B5. While E. coli O55: B5 LPS has been used as an example, the method of this invention may be used to produce antigens and antibodies for other microorganisms containing endotoxin. In addition, the method of producing the antigen results in a purified product in an efficient, cost effective manner. Further, the diagnostic tests using the LPS and/or antibodies specific for the endotoxin allows assay of complex biological materials without any purification and no interference from foreign materials, with highly sensitive results.

Whereas particular embodiments of the invention have been described above for purposes of illustration, it will be evident to those skilled in the art that numerous variations of the details may be added without departing from the invention as defined in the appended claims.

We claim:

1. An antigen comprising a lipopolysaccharide-polymyxin B-matrix complex, wherein said lipopolysaccharide is obtained from a Gram-negative bacterium that contains endotoxin.

2. The antigen of claim 1, wherein said matrix is characterized by being insoluble in an aqueous medium and is bound to said polymyxin B.

3. The antigen of claim 2, wherein said matrix is selected from the group consisting of synthetic, natural, and polymeric materials.

4. The antigen of claim 3, wherein said matrix is selected from the group consisting of polyethylene, polypropylene, polystyrene, cellulose, nitrocellulose, dextran, glass fibers, asbestos fibers, agarose, and nylon.

5. The antigen of claim 4, wherein said matrix is agarose.

6. An antigen comprising a lipopolysaccharide-polymyxin-B-matrix complex, wherein said lipopolysaccharide is obtained from a Gram-negative bacterium that contains endotoxin, said antigen induces antibodies specific for endotoxin.

7. The antigen of claim 1, wherein said organism is a Gram-negative bacterium.

8. The antigen of claim 7, wherein the lipopolysaccharide is isolated from a bacterium selected from the group consisting of Escherichia coli, Salmonella minnesota, Pseudomonas syringe, Enterobacter agglomerans, and Klebsiella pneumonia.

* * * * *

UNITED STATES PATENT AND TRADEMARK OFFICE
CERTIFICATE OF CORRECTION

PATENT NO. : 4,870,158
DATED : September 26, 1989
INVENTOR(S) : MERYL H. KAROL and LISA K. RYAN It is certified that error appears in the above-identified patent and that said Letters Patent is hereby corrected as shown below:

Column 3, line 13, --produces-- should be inserted after "that".

Column 3, line 26, "ot" should be --of--.

Column 5, lines 52-53, "phosphates" should be --phosphatase--.

Column 6, line 3, "phosphates" should be --phosphatase--.

Column 6, line 20, "andotoxin" should be --endotoxin--.

Column 7, line 19, "Fir" should be --For--.

Column 7, line 27, --of-- should be inserted before "LPS".

Column 8, line 36, "1:1:" should be --1:10--.

Claim 8, column 10, line 65, "syringe" should be --syringae--.

Signed and Sealed this

Fourteenth Day of May, 1991

Attest:

HARRY F. MANBECK, JR.

Attesting Officer

Commissioner of Patents and Trademarks